United States Patent [19]

Grier et al.

[11] 4,342,872

[45] Aug. 3, 1982

[54] 2-(SUBSTITUTEDPIPERIDYLMETHYL) PROPENE AND PROPANE NITRILES

[75] Inventors: Nathaniel Grier, Englewood; Richard A. Dybas, Somerville; Bruce E. Witzel, Rahway, all of N.J.

[73] Assignee: Merck & Co., Inc., Rahway, N.J.

[21] Appl. No.: 194,489

[22] Filed: Oct. 6, 1980

Related U.S. Application Data

[60] Division of Ser. No. 8,985, Feb. 5, 1979, Pat. No. 4,274,700, which is a continuation-in-part of Ser. No. 795,693, May 11, 1977, abandoned.

[51] Int. Cl.³ .......................................... C07D 401/06
[52] U.S. Cl. .................................. 546/186; 546/242; 546/246; 546/214; 546/209; 546/247; 424/267

[58] Field of Search ....................... 546/242, 243, 186

[56] References Cited

U.S. PATENT DOCUMENTS 4,247,700  1/1981  Grier et al. ..................... 546/246

Primary Examiner—Robert T. Bond
Attorney, Agent, or Firm—Raymond M. Speer

[57] ABSTRACT

Antimicrobial agents suitable for use in aqueous systems for their preservation against biodeterioration include substitutedpiperidinomethylpropenenitriles and propanenitriles. The unsaturated compounds are prepared by reaction of a suitable piperidine with cyano acetic acid and formaledehyde: the propane derivatives therefrom by nucleophilic addition.

4 Claims, No Drawings

2-(SUBSTITUTEDPIPERIDYLMETHYL) PROPENE AND PROPANE NITRILES

This is a division of application Ser. No. 008,985, filed Feb. 5, 1979, now U.S. Pat. No. 4,274,700 issued Jan. 27, 1981, which was a continuation-in-part of Ser. No. 795,693, filed May 11, 1977, now abandoned.

The compounds of this invention are broad spectrum antimicrobial agents and have the structure:

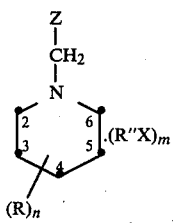

where Z is

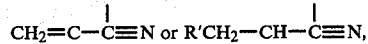

R is in the 2-, 3-, or 4-positions and is loweralkyl; arlow- eralkyl; aryl; loweralkylene; alicyclic; alicyclicloweral- kyl; heteroalicyclic; heterocyclic; heterocyclicalkyl; carboxy; loweralkoxycarbonyl; loweralkylcarbonyl; carbamyl; hydroxy; halo; phenyl; hydroxyalkyl; N-loweralkylcarbamyl; n is an integer of 1 to 4; and R may be the same of different; and R' is

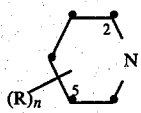

where R is as previously defined, or R' is amino, lowe- ralkylamino, diloweralkylamino, piperidino, hydroxy, loweralkoxy and m is the integer 0, 1 or 2 where R" is hydrogen, $C_1$-$C_{18}$ alkyl, benzyl and X is a suitably charged anion.

The term "loweralkyl" includes $C_{1-6}$ saturated hydrocarbons such as methyl, ethyl, propyl, isopropyl, butyl, t-butyl, isobutyl, pentyl and hexyl.

The term "halo" includes chloro, fluoro, bromo and iodo.

Where R is alkylene, n is 1 and the alkylene moiety bridges two similar groups

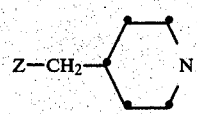

to provide bis compounds of the structure:

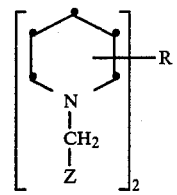

Suitable anions include anions derived from inorganic acids as well as those or organic acids such, for example, as halide, e.g., chloride, bromide or iodide or sulfate, bisulfate, nitrate, phosphate, acetate, propionate, maleate, succinate, laurate, oleate, palmitate, stearate, ascorbate, gluconate, citrate, carbonate, bicarbonate, benzoate, salicylate, pamoate, phthalate, furoate, picolinate, dodecylbenzenesulfonate, laurylethersulfate, nicotinate and the like.

As used herein the term "lower" is intended to define a moiety of from 1 to 6 carbon atoms, and especially a moiety of from 1 to 4 carbon atoms. Also, piperidinomethyl and 1-piperidylmethyl refer to the same moiety, that is,

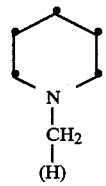

where (H) can be replaced by other substituents.

The preferred embodiments of this invention are those compounds in which n is 1 and R is hydroxy or hydroxyloweralkyl, carbamyl, N-loweralkylcarbamoyl, carboxy, loweralkoxycarbonyl, loweralkyl, loweralkylene, and R' is diloweralkylamino, loweralkyl, loweralkylene. Specific examples of such compounds are:
2-(3-hydroxypiperidinomethyl)propenenitrile
2-(4-hydroxypiperidinomethyl)propenenitrile
2-(3-hydroxymethylpiperidinomethyl)propenenitrile
2-(4-hydroxymethylpiperidinomethyl)propenenitrile
2-[4-(N-butylcarbamyl)piperidinomethyl]propenenitrile
2-(4-fluoropiperidinomethyl)propenenitrile
2-(3-chloropiperidinomethyl)propenenitrile
2-[3-(N-butylcarbamyl)piperidinomethyl]propenenitrile
2-(3-acetylpiperidinomethyl)propenenitrile
2-(4-acetylpiperidinomethyl)propenenitrile
2-(4-carboxypiperidinomethyl)propenenitrile
2-(3-carboxypiperidinomethyl)propenenitrile
2-(4-carbamylpiperidinomethyl)propenenitrile
2-(3-carbamylpiperidinomethyl)propenenitrile
2-(4-hydroxypiperidinomethyl)propenenitrile benzyl bromide quaternary salt
2-(3-hydroxypiperidinomethyl)propenenitrile methyl iodide quaternary salt
2-(4-isopropylpiperidinomethyl)propenenitrile
2-(3-isopropylpiperidinomethyl)propenenitrile
2-(4-hydroxy-4-phenylpiperidinomethyl)propenenitrile
2-(3-hydroxy-3-phenylpiperidinomethyl)propenenitrile
2-(3-cyclopentylpiperidinomethyl)propenenitrile
2-(4-cyclopentylpiperidinomethyl)propenenitrile
2-(4-cyclohexylmethylpiperidinomethyl)propenenitrile
2-(3-cyclohexylmethylpiperidinomethyl)propenenitrile 2-cyano-1-(4-hydroxymethylpiperidino)-3-piperidino propane
2-cyano-1-(3-hydroxymethylpiperidino)-3-piperidino propane
2-cyano-1,3-di-(4-hydroxypiperidino)propane
2-cyano-1,3-di-(3-hydroxypiperidino)propane
2-cyano-1-dimethylamino-3-(3-hydroxymethyl-piperidino)propane
2-cyano-1-dimethylamino-3-(4-hydroxymethyl-piperidino)propane
2-cyano-1-(4-t-butylpiperidino)-3-(3-hydroxymethyl-piperidino)propane
2-cyano-1-hydroxymethyl-3-(4-isopropylpiperidino)propane
2-cyano-1-methoxymethyl-3-(4-fluoropiperidino)propane
2-cyano-1-butoxymethyl-3-(4-phenyl-4-hydroxypiperidino)propane
2-cyano-1-dimethylamino-3-(4-hydroxypiperidino)propane
2-cyano-1-dimethylamino-3-(3-hydroxypiperidino)propane
2-cyano-1-dimethylamino-3-(4-carbamylpiperidino)propane
2-cyano-1-dimethylamino-3-(3-carbamylpiperidino)propane
2-cyano-1-(4-hydroxypiperidino)-3-piperidinopropane
2-cyano-1-(3-hydroxypiperidino)-3-piperidinopropane
bis-2-[4,4'-(1,3-trimethylene)-1,1'-dipiperdyl]methylpropenenitrile
bis-2-[4,4'-(1,6-hexamethylene)-1,1'-dipiperdyl]methylpropenenitrile
2-(2-methylpiperidinomethyl)propenenitrile
2-(4-methylpiperidinomethyl)propenenitrile
2-(3-isopropylpiperidinomethyl)propenenitrile
2-(4-t-butylpiperidinomethyl)propenenitrile
2-(4-n-hexylpiperidinomethyl)propenenitrile
2-(4-piperidinopiperidinomethyl)propenenitrile
2-[4-(tetrahydrofuran-2-yl)piperidinomethyl]propenenitrile
2-(3-benzylpiperidinomethyl)propenenitrile
2-[4-(thiazol-2-ylmethyl)piperidino]propenenitrile Surprisingly, the varied substituents on the piperidine ring which assist in optimizing antimicrobial efficiencies are predominantly electronwithdrawing. However, the alicyclicalkyl example and others described below of the lipid-like electron donating species substitution products also serve to provide strongly inhibitory action. Moreover, practically all of these compounds assayed in a nitrient agar medium demonstrate a relatively low order of potency against gram positive, gram negative bacteria and fungi. In relatively complex industrial media such as aqueous paints or oil recovery pusher fluids, they can prevent microbial degradation at very low concentrations, surpassing in efficiency many of the better commercially used inhibitors.

The propenenitrile derivatives are synthesized as follows:

I.

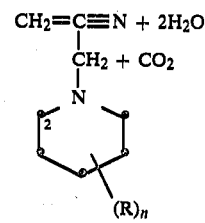

The 2-cyano-1,3-disubstituted propanes are obtained from the propene nitriles by nucleophilic addition:

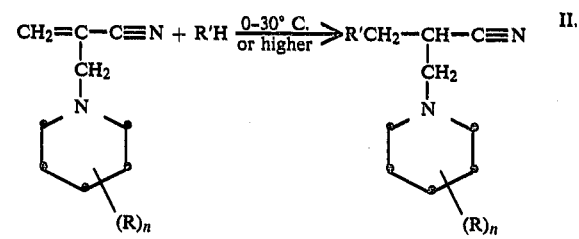

II.

where $R_n$ and $R'$ are as previously defined.

Substituted piperidines are available chemically by a variety of methods. An extensive review of such procedures may be found in "Heterocyclic Compounds", Vol. I, R. C. Elderfield, Editor, John Wiley and Sons, Inc., New York (1950), p. 631–676. Pyridine compounds may be reduced to the piperidines with sodium in lower alkanols, with tin and hydrochloric acid or by catalytic hydrogenation with nickel or noble metal catalysts. Generally, the pyridines substituted with a variety of groups are more easily reduced then the unsubstituted pyridine.

For example, 4-hydroxypiperidine can be prepared according to the method of E. E. Mikhlina, V. Ya. Vorobeva and M. V. Rubtsov [Zhur. Obschei Khim. 30 1885-93 (1960)] by the reduction of 4-piperidone hydrochloride with sodium borohydride in ethyl alcohol using ice cooling in 61% yield.

Various loweralkyl substituted piperidines can be synthesized following the procedures of J. LaKomy, A. Silhankova, M. Ferles and O. Exner [Collection Czechoslov. Chem. Commun., 33, 1700–1708 (1968)]. 3-Isopropylpiperidine was prepared by the sodium reduction of 3-isopropylpyridine in boiling ethyl alcohol; 4-isopropylpiperidine by the electrolytic reduction of dimethyl-4-pyridylcarbinol and subsequent catalytic hydrogenation with Adams platinum; cis and trans-2,4-dimethylpiperidine from the sodium reduction in butyl alcohol of 2,4-lutidine. Many polyalkylated pyridines are commercially available either from coal tar or by total synthesis. The compounds are readily converted to the corresponding piperidines using either chemical or catalytic reduction methods well known in the art.

4-Chloropiperidine is obtained from 4-hydroxypiperidine by reaction with supersaturated hydrochloric acid for 12 hours at 140° C. according to the method of R. Fankhauser, C. A. Grob and V. Krasnobajew, [Helv. Chim. Acta., 49, 690–695 (1966)]. 4-Chloro-2,2,6,6-tetramethylpiperidine is obtained similarly from the 4-hydroxy derivative. Hydrogenation of triacetone amine in ethyl alcohol with Adams platinum catalyst provides the tetramethylated hydroxypiperidine. 2,5-Dimethyl-4-piperidinol and 2,5-dimethyl-4-ethyl-4-piperidinol may be prepared according to the methods of I. N. Nazarov, A. S. Shatif Kanov, S. A. Yasupov and T. G. Sarbaev [Zhur. Obschei Khim., 30, 3267-71 (1960)].

Generally, the reaction as illustrated by equation I is run using equimolar quantities of a substituted piperidine and cyanoacetic acid with two moles or more of formaldehyde in homogeneous solution such as with dioxane. The initiation of product formation, usually beginning after 15 minutes is marked by evolution of carbon dioxide and completion obtained after three hours. Occasionally, reaction times as long as 30 hours at 25°-35° C. are required for total conversion. It is useful for good control to precool the cyanoacetic acid in dioxane solution to 5°-15° C., gradually add the piperidine derivative with the cold bath applied and finally the formaldehyde. After all has been added, the ice bath is removed and the solution allowed to warm.

The work-up involves stripping off the solvent at 40° C./15 mm., taking up the residue in ether and washing with cold aqueous 5% potassium carbonate followed by ice water. The ether solution is then dried over anhydrous magnesium sulfate, filtered and volatiles removed to an internal temperature of 40°-50° C. at 15 mm. The residue is further purified preferably by fractional distillation under reduced pressure. Often, the quality is sufficiently high to permit use as isolated.

The 2-cyano-1,3-disubstituted propanes are prepared in accordance with the chemical scheme of equation II. For those products in which the substituted piperidino groups at the 1 and 3 carbon atoms of the 2-cyanopropanes are identical, a change in molar reactant ratios from 1 mole of ring substituted piperidine to 2 moles per mole of cyanoacetic acid and per 2 moles of formaldehyde will provide the compounds in one process step.

The sequence of steps may be postulated as depicted by equations I and II, wherein R'H is simply second mole of

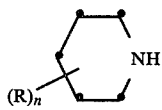

where R, R' and n are as above defined. When R'H is to be different, then the unsaturated nitrile products of equation I may be dissolved in dioxane, mixed with a 5-25% molar excess of the compound R'H, which may be previously dissolved in the same volume of water or dioxane, and allowed to stand at 20°-35° C. until addition is complete. Disappearance of the double bond, as measured by a change in infrared absorption or loss of the vinyl protons in the nuclear magnetic resonance spectrum, is used to monitor the progress of the reaction. Dry, powdered potassium carbonate is then added to saturation and the mixture extracted with ether. After filtration of the separated organic phase and drying over anhydrous magnesium sulfate, the solvent is stripped and the residue purified by fractional distillation under reduced pressure.

The compounds of this invention are useful in the protection of aqueous systems such as aqueous paints, adhesives, pigment dispersions, emulsions, cooling tower waters, enhanced oil recovery brines and pusher fluids, papermill white water, and metal-working fluids against microbial deterioration.

For use, these compounds can be applied neat or employed in a diluted form. Satisfactory diluents include any inert material not destructive of the antimicrobial activity and especially liquid formulations comprising aqueous dispersions, solutions, and emulsions. Solid diluents include talc, corn starch, alumina and diatomaceous earth. The antimicrobial agents of this invention can also be deposed on materials such as natural fibers including paper, cotton, wool and synthetic fibers such as nylon, polypropylene, as well as upon inanimate surfaces including hard surfaces such as wood, glass, metal, tile, rubber, plastic, and porous surfaces such as concrete, leather and the like.

For agricultural uses, the compounds of the invention are most suitably used in the form of aqueous suspensions or emulsions, the free base products being generally insoluble in water. For this type of formulation various powdered carriers can be employed to aid in achieving uniform distribution. Talc, fuller's earth, calcium silicate, calcium carbonate, clays and the like are admixed with the agent along with wetting and dispersing agents and sticking agents. For maximum chemical compatability those which are non-ionic in character are preferred. Other anionic or cationic surfactants are also satisfactory.

In formulating the compounds of this invention for the above uses, these compounds can be employed in combination with other antimicrobial agents, surfactants, insecticides, defoamers, odorants, or as chelates of metals such as copper, calcium, magnesium and iron.

Two aqueous paints, an interior polyvinyl acetate and an exterior polyacrylic were studied as vulnerable substrates. An inoculum prepared from a 24 hour old broth culture of Pseudomonas aeruginosa ATCC 10145 was used at a rate of 1 ml. per 100 gm. of paint. The inoculated samples are incubated at 28°-30° C. and samples are assayed for microbial population densities after 24, 48, 72 hours and seven days by streaking on tryptone glucose extract agar plates. These plates are incubated at 28°-30° C. for seven days and examined for growth. Seven days after the first inoculation, the paints are reinoculated and the assay scheme repeated. Samples which are rendered sterile within 24-72 hours upon microbial challenge and which remain so after seven days and on repeat challenge are adequately protected.

Typical results indicate that compounds of this invention containing 3-hydroxy, 3-hydroxymethyl, 4-hydroxy, 4-fluoro, 4-carboxy substituted piperidino derivatives and others can produce sterility at concentrations of 0.01-0.1% by weight of both paints within 24-72 hours upon inoculation and reinoculation. Control paints containing no preservatives are completely degraded at the end of the two-week period.

The two aqueous paint systems have the compositions of Tables 1 and 2 and were selected as representative of the more commonly manufactured types. The addition of other agents including different thickeners, pigments and extenders, paint film antifungal agents, surfactants, etc., does not adversely affect the performance of the compounds invented herein.

TABLE 1

| PVA EXTERIOR (COMPOSITION - PARTS BY WEIGHT) | |
|---|---|
| Cowles dispenser: | |
| Water | 140 |
| Daxad 30, Na salt of polymerized carboxylic acid, W. R. Grace Co. | 6 |
| Potassium tripolyphosphate | 1 |
| Igepal Co-630, nonylphenoxypoly-(ethyleneoxy)ethanol, General Aniline & Film Co. | 1.5 |
| Polyethyleneglycol | 2 |

TABLE 1-continued
PVA EXTERIOR (COMPOSITION - PARTS BY WEIGHT)

| | |
|---|---|
| Methylcellulose solution (3%) | 70 |
| Defoamer | 1 |
| 2(4'-thiazolyl)benzimidazole | 1 |
| Titanium dioxide | 250 |
| Disperse ten minutes at 4,800 r.p.m. | |
| Talc | 75 |
| Disperse ten minutes at 4,800 r.p.m. | |
| Reduction: | |
| Methylcellulose solution (3%) | 68.5 |
| Methyl carbitol | 30 |
| Ethylene glycol | 40 |
| Polyvinyl acetate emulsion | 425 |

TABLE II
INTERIOR ACRYLIC (COMPOSITION - PARTS BY WEIGHT)

| | |
|---|---|
| Cowles disperser: | |
| Water | 450 |
| Diethylene glycol[1] | 30 |
| Methylcellulose, 4,000 cps[1] | 5 |
| Potassium tripolyphosphate | 1.66 |
| Lecithin | 4 |
| Defoamer | 3 |
| Titanium dioxide | 125 |
| Disperse ten minutes at 4,800 r.p.m. | |
| Talc | 250 |
| Calcium silicate | 5 |
| Disperse ten minutes at 4,800 r.p.m. | |
| Reduction: | |
| Acrylic resin emulsion | 208 |

[1]Premix diethylene glycol and methylcellulose prior to adding water.

A surprising finding was made in the aqueous paint preservation tests by comparing the relative efficiency of the known 2-morpholinomethylpropene-nitrile (A) with the novel 2-(4-hydroxypiperidinomethyl)-propenenitrile (B) or the known nor-hydroxy compound (C). Compound (A), in which an oxygen atom is ring inserted, appears incapable of eliminating destructive microorganisms even after 168 hours and at concentrations twenty-fold and greater than compounds (B) and (C), which produce sterility in 24 hours at 0.01% by weight concentrations in the aqueous systems. The lack of activity of (A) extends to other vulnerable substrates as well.

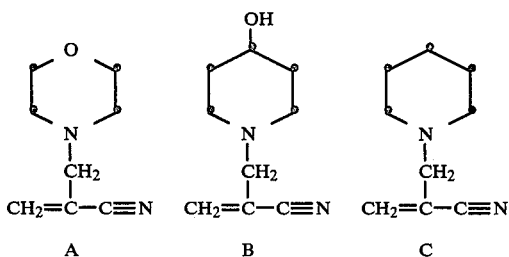

EXAMPLE 1
2-(1-Piperidylmethyl)propenenitrile

Cyanoacetic acid (51 g., 6 mole) was dissolved in 150 ml. of dioxane, the solution cooled to 5° C. and piperidine (53 g., 0.6 mole) dripped in while maintaining the temperature at 10°-15° C. Then, 37% aqueous formaldehyde (109.5 g., 1.35 mole) was slowly added at 0°-10° C. After two hours, the ice bath was removed and the mixture stirred overnight at 20°-25° C. It was then stripped at 15 mm. pressure and bath temperature of 48° C. The residue was chilled, mixed with 100 ml. of ether, saturated with sodium chloride and the ether layer separated. This extract was washed with two 25 ml. portions of cold 5% aqueous potassium carbonate and finally with 10 ml. of ice water. The ether solution was dried over anhydrous magnesium sulfate, filtered, stripped and fractionated using a Vigreux column. The fraction boiling at 86°-88° C./2 mm. was of practically analytical quality, 40.8 g., $R_f$ 0.66 on silica gel using chloroform-methyl alcohol (90:10) development. This is, however, a known compound.

EXAMPLE 2
2-(4-Fluoro-1-piperidylmethyl)propenenitrile

4-Fluoropiperidine (0.7 g., 0.005 mole) was dissolved in a mixture of 3 ml. of dioxane and 2 ml. of water containing cyanoacetic acid (0.43 g., 0.005 mole). The solution was heated to 65° C. and carbon dioxide evolution began. It was maintained at 60°-65° C. for 2½ hours and allowed to stand overnight. A solid gummy residue, 1 gm., was obtained upon stripping in a bath at 55° C. and at 1 mm. It was taken up in a small amount of water, made alkaline with sodium bicarbonate and extracted with ether. The organic layer was water washed and dried over anhydrous sodium sulfate. After solvent stripping, the product was obtained as a colorless oil, 0.7 g., of analytical purity.

EXAMPLE 3
2-(4-Hydroxy-1-piperidylmethyl)propenenitrile

Cyanoacetic acid (8.5 g., 0.1 mole) was dissolved in 25 ml. of dioxane. 4-Hydroxypiperidine (10.1 g., 0.1 mole) was added within two minutes; the resultant slurry temperature rose to 33° C. After 1 hour of mixing, 37% aqueous formaldehyde (17 g., 0.2 mole) was run in over a 12 minute period. The temperature rose to 38° C. and carbon dioxide evolved steadily. All was in solution after about one-half of the formaldehyde was added and an additional twelve hours was used to complete the reaction. It was then stripped using a bath at 46° C. and 1-5 mm. of pressure. The residual oil, 17 g., was taken up in methylene chloride, washed with water, dried and stripped to leave 8.1 g. of nearly colorless product, b.p. 125° C./1 mm.

Methiodide Quaternary salt of 2-(4-hydroxy-1-piperidylmethyl)propenenitrile

The title base (1.66 g., 0.01 mole) was dissolved in 25 ml. of dry ether and mixed with 0.7 ml. methyl iodide. On stirring overnight, a yellow oily film was evident. An additional 1.0 ml. of methyl iodide was added and reacted overnight. A solid formed which after removal of ether by decantation and further ether washing was dried under vacuum; yield, 1.5 g. of a pale yellow solid m.p. 169°-173° C. with decomposition. It is non-hygroscopic and analytically pure.

Benzyl Bromide Quaternary Salt of 2-(4-Hydroxy-1-piperidylmethyl)propenenitrile 2-(4-Hydroxy-1-piperidylmethyl)propenenitrile (1.66 g., 0.01 mole) was dissolved in 15 ml. of acetone and mixed with benzyl bromide (1.9 g., 0.011 mole). The solution was heated in a bath at 70° C. for 12 hours, a white precipitate formed. The product was washed with acetone followed by ether and then dried at 45° C. under vacuum; yield, 2.8 g., m.p. 183°-185.5° C.

Other quaternary salts may be synthesized using n-butyl bromide, n-dodecyl chloride, 2-ethylhexyl bromide hexadecyl bromide, phenethyl bromide following this procedure.

Acid salts such as the hydrochloride, sulfate, phosphate, nitrate, bromide are obtained simply upon the addition of aqueous solution in slight theoretical excess to aqueous alcohol solutions of the free base substituted piperidinomethyl propene and propane nitriles. The salts can be isolated by removing the solvents at ambient temperature and under reduced pressure or generally by precipitation using acetone. The anion such as chloride, bromide, or nitrate may be exchanged for dodecylbenzene sulfonate, laurylether sulfate and the like by metathetical reaction with the sodium salt in aqueous alcohol. Alternatively, ion exchange using resins, a well known technique, may also be employed.

EXAMPLE 4

2-[(3-Hydroxymethyl-1-piperidyl)methyl])propenenitrile

Cyanoacetic acid (25.5 g., 0.3 mole) was dissolved in 75 ml. of dioxane, cooled to 0°–10° C., and with the cooling bath in place, 3-piperidinemethanol (34.5 g., 0.3 mole) dripped in. The temperature then rose upon the addition of 37% aqueous formaldehyde (50 g., 0.6 mole) to 30° C. with the cold bath removed. After mixing overnight at room temperature, the mixture was concentrated in a rotary evaporator, saturated with sodium chloride and extracted with ether. The organic phase was washed with sodium carbonate solution, dried and concentrated. The residue yielded 43.8 g.; 38 g. was fractionally distilled and the product isolated, 22.4 g., b.p. 137° C./0.4 mm.

EXAMPLE 5

2-[(4-t-Butyl-1-piperidyl)methyl]propenenitrile

Cyanoacetic acid (1.75 g., 0.02 mole) was dissolved in 10 ml. of dioxane. In a five minute period 4-t-butylpiperidine (2.8 g., 0.02 mole) was added, the temperature rose to 25° C. from 15° C. obtained by prior cooling with an ice bath. The mixture which solidified became fluid upon the addition of 37% aqueous formaldehyde (3.6 g., 0.04 mole), the temperature rose to 30° C. and carbon dioxide evolution began. The mixture was stirred an additional 12 hours, was taken up in ether and the organic phase separated and washed with water. The dried ether solution was stripped of solvent to leave a solid residue product, 3.7 g. of practically analytical purity. In place of 4-t-butylpiperidine, the use of 2-methylpiperidine (0.02 mole) provided 2-[(2-methyl-1-piperidyl)methyl]propenenitrile as a colorless oil, $R_f$ SiO$_2$ 0.58 (5% ethanol in methylene chloride).

EXAMPLE 6

2-[(4-Cyclohexylmethyl-1-piperidyl)methyl]propenenitrile

Cyanoacetic acid (0.9 g., 0.01 mole) was dissolved in 6 ml. of dioxane and 1 ml. of water. In a 15 minute period, 4-cyclohexylmethylpiperidine (1.8 g., 0.01 mole) was added. After an additional 15 minutes, 37% aqueous formaldehyde (1.8 g., 0.02 mole) was dripped in over a two minute period. The reaction mixture was agitated twelve hours at 20°–25° C., extracted with 200 ml. of ether, water washed, dried over anhydrous sodium sulfate, filtered and stripped. A yield of 1.2 g. of high purity product was obtained as a residue.

EXAMPLE 7

2-[(4-Hydroxy-4-phenyl-1-piperidyl)methyl]propenenitrile

A solution of cyanoacetic acid (4.3 g., 0.05 mole) in 15 ml. of dioxane was cooled with an ice bath, and 4-hydroxy-4-phenylpiperidine (8.8 g., 0.05 mole) added while maintaining an internal temperature of 20°–25° C. Upon complete addition and a further fifteen minutes of stirring 37% aqueous formaldehyde (9 gm., 0.10 mole) was added dropwise in approximately five minutes. When approximately half was added carbon dioxide evolution was observed, the maximum internal temperature was 28° C. The reaction mixture was stirred overnight, mixed with 100 ml. of methylene chloride, the organic phase separated, washed with water and salt solution. Upon removal of solvent the product was obtained as an oil, 10.5 g., in practically analytical purity.

EXAMPLE 8

1-(2-Cyano-2-propenyl)-4-piperidinecarboxamide

Cyanoacetic (9 g., 0.1 mole) was dissolved in 30 ml. of dioxane and 5 ml. of water. Isonipecotamide (12.8 g., 0.1 mole) was then added followed by an additional 10 ml. of water to provide nearly total dissolution. Finally, 37% aqueous formaldehyde (18 g., 0.22 mole) was added within three minutes and the internal temperature rose to 35° C.; vigorous gassing ensued. The reaction mixture was stirred twelve hours and then stripped using a rotary evaporator at 15 mm. pressure. The solid residue was taken up in 100 ml. of methylene chloride, washed with 100 ml. of water, dried over anhydrous magnesium sulfate, and then stripped to a solid residue, 7.5 g., m.p. 127°–129° C., which was analytically pure.

EXAMPLE 9

N-(n-Butyl)-1-(2-cyano-2-propenyl)-4-piperidinecarboxamide

Cyanoacetic acid (0.9 g., 0.01 mole) was dissolved in 11 ml. of dioxane and 4 ml. of water. N-butyl isonipecotamide (1.84 g., 0.01 mole) was added with stirring in portions to keep the temperature below 30° C. In 2 minutes 37% aqueous formaldehyde (1.66 g., 0.02 mole) was added and the temperatures maintained at 25°–28° C. Carbon dioxide evolution was evident. After 4 hours, the reaction appeared complete as determined by thin layer chromatography on silica gel developed with chloroform-methyl alcohol (95:5). The solvents were removed by stripping at 35° C./15 mm. and the residue taken up in 100 ml. methylene chloride. The organic phase was washed with water, dried and stripped to yield 1.7 g. of product, analytically pure.

EXAMPLE 10 bis-2-[4,4'-(1,3-Trimethylene)-1,1'-dipiperidyl]-methylpropenenitrile

Cyanoacetic acid (8.5 g., 0.1 mole) was dissolved in 45 ml. of dioxane. The 4,4'-trimethylenedipiperidine (10.5 g., 0.05 mole) was added. The temperature rose to 31° C. with precipitation of the salt. Partial solution was obtained by the addition of 10 ml. of water. In 10 minutes, 37% aqueous formaldehyde (18 g., 0.2 mole) was dripped in. The exotherm resulted in a temperature climb to 41° C. The two phase reaction mixture was stirred an additional 12 hours at 25°-30° C. The mixture was concentrated to a solid residue by stripping under vacuum. It was mixed with ether, washed with water and the organic phase dried over anhydrous sodium sulfate. The filtered solution was stripped using a bath temperature of 40°-43° C. and 1 mm. finally. The residue crystallized on cooling to room temperature; yield, 16.4 g. In place of 4,4'-trimethylenedipiperidine, 3,3'-(1,6-hexamethylene)dipiperidine and 4,4'-(2-methyl-1,4-tetramethylene)dipiperidine.

EXAMPLE 11

2-(4-Carboxy-1-piperidylmethyl)propenenitrile

Cyanoacetic acid (12.8 g. 0.15 mole) was dissolved in 25 ml. of dioxane. Next, isonipecotic acid (19.4 g., 0.15 mole) was added. Then, 37% aqueous formaldehyde (25 g., 0.3 mole) was dripped in and the temperature maintained at a maximum of 35° C. After mixing overnight sodium chloride was added to saturation and methylene chloride used to extract the mixture. The organic phase was washed with water, dried over anhydrous sodium sulfate and after filtration, concentrated. Most of the product appeared in the aqueous phase. This was extracted twice with 500 ml. of methylene chloride in a continuous extractor. The residue obtained after solvent removal weighed 14.2 g., m.p. 109°-111° C. of analytical purity.

EXAMPLE 12

2-(4-Carboethoxy-1-piperidylmethyl)propenenitrile

Cyanoacetic acid (8.6 g., 0.1 mole) was dissolved in 35 ml. of dioxane. 4-Carboethoxypiperidine (15.7 g., 0.1 mole) was added a precipitate rapidly formed. When one-half was added 10 ml. of water was then admixed and the temperature controlled below 24° C. until complete addition. With ice bath cooling, 37% aqueous formaldehyde (18 g., 0.2 mole) was dripped in over an 8-minute period and the temperature allowed to rise to 29° C. accompanied by vigorous carbon dioxide evolution. Two phases separated and stirring was continued for an additional 12 hours. After concentration in a bath at 45° C. and under reduced pressure, 22.4 g. of an oil resulted. The product was distilled, b.p., 130°-132° C./0.6 mm., yield, 16.3 g.

EXAMPLE 13

2-Cyano-1-dimethylamino-3-(4-hydroxypiperidino)propane

2-Dimethylaminomethylpropenenitrile (1.1 g., 0.01 mole) was cooled to 10°-15° C. and to it was added dropwise 4-hydroxypiperidine (1.0 g., 0.01 mole). The evolution of heat is observed. The homogeneous mixture is allowed to stand 12 hours at 15°-20° C. Completion of addition reaction is determined using thin layer chromatography on silica gel with benzene-methyl alcohol (90:10) development. The appearance of a single spot and elimination of reactant spots indicate termination.

Similarly, 2-hydroxymethylpropenenitrile, 2-piperidinomethylpropenenitrile, 2-(4-hydroxypiperidino)propenenitrile, 2-aminomethylpropenenitrile, 2-methylaminomethylpropenenitrile, 2-methoxymethylpropenenitrile and other R' containing 3-substituted-2-methylenepropanenitriles may be used for the addition reaction with substituted piperidines as defined by

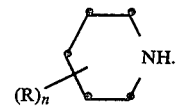

Generally, equimolar quantities of reactants are employed as illustrated without solvent and at 10°-25° C. Inert solvents which are suitable may be water, dioxane, methylene chloride, isopropyl alcohol and mixtures of these. It is also possible to use as reactants the propenenitriles of this invention and add the R'H reactant as defined following the conditions outlined in this example.

The compounds of this invention appear to have potent antiinflammatory properties. One manifestation, which correlates well with beneficial therapeutic action in human, is the ability to surpass swelling or prevent it in the rat paw edema assay with carageenan as the inciting agent upon local injection. The compounds may be administered orally, intraperitoneally or by other well known methods in dosages as low as several milligrams per kilogram of animal body weight and at the upper range of maximal tolerability; this may be from 10 to 100-fold greater than the lowest dosage which produces a positive response. They may be given orally as liquids, powders, suspensions with pharmaceutical carriers, parenteral administration in the form of solutions and emulsions may be used. Other dosage forms include vaginal and rectal suppositories, subcutaneous implants, topical ointments and the like.

The daily dose level will depend upon the severity of the disease and the reaction sensitivity of the patient. The regimen may vary from 5-500 milligrams per day and should be evaluated and monitored individually.

What is claimed is:

1. A compound of the formula:

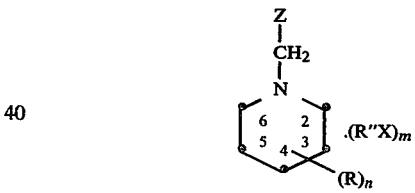

where Z is

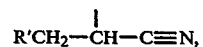

where R" is hydrogen, $C_1$-$C_{18}$ alkyl, benzyl, phenethyl; R is in the 2-, 3-, or 4-positions and is hydroxy or hydroxyalkyl; R' is

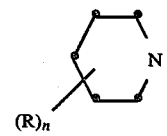

where R is as previously defined, or
R' is piperidino;
n is the integer of 1 to 4;
m is the integer 0 or at least 1; and
X is a suitably charged anion.
2. A compound according to claim 1 where m is 0.
3. A compound according to claim 2 where n is 1.
4. A compound according to claim 2 where R' is piperidino and where n is 1.

* * * * *